Figure 1:
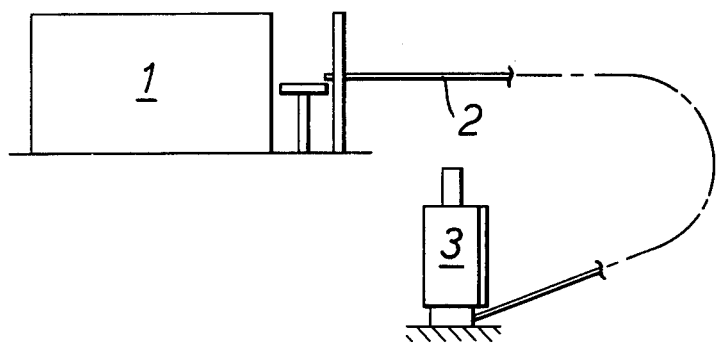

United States Patent [19]

Ambrose et al.

[11] 3,942,892
[45] Mar. 9, 1976

[54] APPARATUS AND METHOD FOR THE SPECTROSCOPIC ANALYSIS OF SOLID METAL ARTICLES

[75] Inventors: Alan Douglas Ambrose, Corby; Samuel Muir, Near Market Harborough, both of England

[73] Assignee: British Steel Corporation, London, England

[22] Filed: July 8, 1974

[21] Appl. No.: 486,554

[52] U.S. Cl. ................................. 356/86; 250/227
[51] Int. Cl.² ........................................... G01J 3/30
[58] Field of Search .............. 356/86, 187; 250/227

[56] References Cited
UNITED STATES PATENTS

| | | | |
|---|---|---|---|
| 3,633,990 | 1/1972 | Baierlein | 356/86 |
| 3,659,944 | 5/1972 | Bojic | 356/86 |
| 3,692,415 | 9/1972 | Shiller | 356/187 |
| 3,791,743 | 2/1974 | Cody et al. | 356/86 |

Primary Examiner—Vincent P. McGraw
Attorney, Agent, or Firm—Nolte and Nolte

[57] ABSTRACT

An arrangement for analysing the metal content of a metal article which includes a portable probe assembly adapted for application to the article to be analysed, a discharge electrode carried by the probe assembly, means for initiating and maintaining an electrical discharge between the electrode and the article, a radiation spectrometer, and a radiation guide connecting the probe assembly to the radiation spectrometer and providing a radiation path from the discharge to the spectrometer to enable spectroscopic analysis by the spectrometer of radiation emitted from the discharge. The probe assembly includes a casing having a mount for facing to the article to be tested, and a spacing member disposed at the mouth of the casing for contacting the article and locating the assembly in relation thereto, the assembly being so disposed and arranged that in operation with the spacing member contacting the article, the electrode is at an optimum discharge spacing from the article.

11 Claims, 2 Drawing Figures

U.S. Patent   March 9, 1976   3,942,892

APPARATUS AND METHOD FOR THE SPECTROSCOPIC ANALYSIS OF SOLID METAL ARTICLES

This invention relates to the analysis of metals and more particularly to the analysis of metals by optical emission spectroscopy.

In plants involved in the production of a range of metal articles, such as steel tubes, possibly having a range of constituent element proportions, it is advantageous to be able to analyse the metal content of the articles so as to check for the correct proportions of constituent elements in the metal.

It has been proposed to do this using optical spectroscopy. In such an arrangement an electrical discharge is struck to a sample surface of metal and light from the discharge is passed into the spectrometer where it is dispersed into its spectrum. The spectrum contains a series of bright lines at various positions along its length generated by the elements present in the sample. The position (wavelength) of a given line identifies the responsible element and the intensity of the line is a measure of the concentration of that element.

A problem with such an analysis system has been that of cutting and preparing suitable samples of metal for mounting in the spectrometer prior to analysis. Clearly this is time consuming and often highly inconvenient under plant conditions.

It is an object of the present invention to overcome this problem.

According to one aspect of the present invention there is provided apparatus for analysing the metal content of a metal article comprising a portable probe assembly adapted for application to the article to be analysed, a discharge electrode carried by the probe assembly, means for initiating and maintaining an electrical discharge between the electrode and the article, a radiation spectrometer, and a radiation guide connecting the probe assembly to the radiation spectrometer and providing a radiation path from the discharge to the spectrometer to enable spectroscopic analysis by the spectrometer of radiation emitted from the discharge, the portable probe assembly including a casing having a mouth for facing to the article to be tested, and a spacing member disposed at the mouth of the casing for contacting the article and locating the assembly in relation thereto, the assembly being so disposed and arranged that in operation thereof with the spacing member contacting the article, the electrode is at an optimum discharge spacing from the article.

According to another aspect of the present invention there is provided a method of analysing the metal content of a metal article comprising the steps of placing a portable probe assembly carrying a discharge electrode against the article such that the discharge electrode is located at an optimum discharge distance from the article, striking an electrical discharge between the electrode and the article, transmitting radiation emitted by the discharge via a radiation guide to a radiation spectrometer, and analysing the output radiation from the radiation guide by the spectrometer.

The electrode may be spring loaded to said optimum discharging spacing from the article. In this case the discharge can be initiated by pressing the electrode into contact with the article and then releasing it so that it is spring urged to its optimum discharge position.

The radiation spectrometer may be an optical spectrometer and the radiation guide an optical light guide.

The light guide may conveniently comprise a flexible guide of optical glass firbes or quartz fibres.

The form of discharge used can be of any kind compatible with safety and the efficient production of light emission containing the spectral rays of the elements to be analysed. Conveniently it can be a high energy low voltage D.C. arc discharge.

Figure 2:
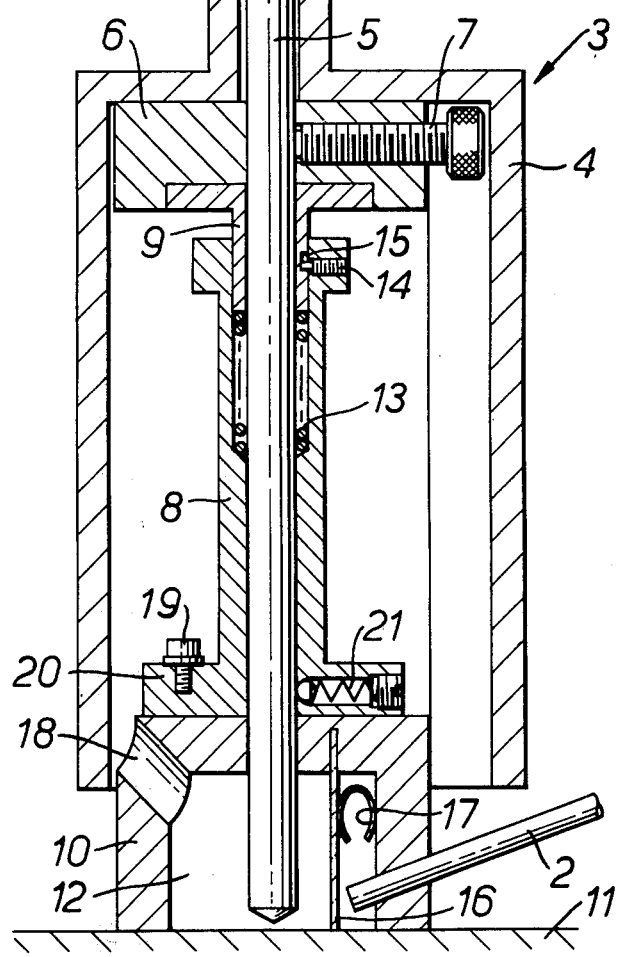

In order that the invention may be more readily understood one embodiment thereof will now be described by way of example with reference to the accompanying drawing in which:

FIG. 1 is a schematic representation of apparatus according to the invention; and FIG. 2 is a sectional elevation of the portable probe assembly of the apparatus of FIG. 1

In FIG. 1 there is illustrated schematically an optical spectrometer 1, connected by means of a flexible optical guide 2 consisting of a plurality of parallel glass fibres to a portable probe assembly 3.

As shown in FIG. 2, the probe assembly 3 includes an insulating casing 4. Mounted within the casing is a discharge electrode 5 of for example thoriated tungsten or copper carried by a mounting block 6 and secured thereto by means of a screw 7. The electrode 5 passes through a tube 8 axially movably mounted on a boss 9 of the block 6. The electrode 5 extends into a spacing member in the form of an inverted cup 10 of insulating material attached to the tube 8.

As can be seen, the open end of the cup 10 contacts in use a metal article to be tested 11 and defines therewith a discharge chamber 12.

The tube 8 is provided with an annular channel surrounding the electrode 5 immediately below the boss 9 within which is disposed a spring 13 which urges the boss 9 block 6 and electrode 5 upwardly. Upward movement thereof is limited by a screw 14 in the tube 8 engaging a slot 15 in the boss 9.

The light guide 2 extends into the discharge chamber 12 and is aligned so as to be directed at the arc gap between the electrode 5 and the article to be tested 11. A removable transparent shield 16, typically of glass or quartz held in place by a spring 17, is located in front of the light guide to prevent any matter sputtered from the arc contaminating the end of the light guide 2. The discharge chamber 12 is provided with a vent 18 for exhaust gases from the arc discharge so arranged as to minimise deposition on the transparent shields.

An electrical terminal screw 19 is provided on a flange 20 of the tube 8, electrical contact between the tube 8 and the electrode 5 being assured by means of a connector assembly 21 in the flange 20.

For operation of the apparatus illustrated, terminal 19 is connected to a positive potential and the article 11 to a negative potential such as to provide a D.C. voltage of approximately 25 to 50 volts on closed circuit between the electrode 5 and the article 11. The electrical power supply may be from a mains source or from a bank of batteries.

The probe assembly is placed on the article in the position shown in FIG. 2.

The casing 4 is then pressed down by hand so that the boss 9 and electrode 5 move axially down the tube 8 until the tip of the electrode 5 contacts the article 11. The casing 4 is then released such as to allow the spring 13 to move the boss 9 and electrode 5 upwardly to the optimum arcing position shown, whereupon a D.C. arc discharge is initiated between the article 11 and electrode 5. Conveniently this arc will be with a current of up to approximately 10 amps, and may for example be at 2 amps.

Light from the arc is passed, via the light guide 2, to the spectrometer 1 for optical analysis.

We have found that the apparatus and method herein described can be applied to metal articles, such as metal tubes, without any particular surface preparation of the article. In this case a delay is desirably provided between the initiation of the arc and commencement of analysis by the spectrometer to permit the arc to burn away surface impurities before testing. We have found that in some cases this delay need only be a few seconds, for example about 5 seconds.

We have found it convenient to use a flexible light guide approximately 10 feet long. However longer guides, for example of more than 16 feet in length, can be used.

Although the light guide specifically referred to is a glass guide, it is possible to use other materials, such as quartz. The advantage of using quartz is the ability of this material to transmit shorter wavelengths, leading to greater analysis possibilities, for example with respect to the carbon content of metals and other elements having preferred spectral emissions in the ultra violet range. 40

Although a light guide with a single end directed into the discharge chamber 12 is illustrated, it is possible to provide a light guide having at least a partial ring of light receiving ends spaced around the discharge chamber in order to increase light transmitted by the guide and to minimise the effect of arc wander. Again the end of the light guide 2 extending into the spectrometer 1 may be shaped for maximum compatibility with the spectrometer inlet.

The spectrometer may be arranged to determine the spectral line intensity (i.e., the concentration of a specific element in the article) by means of photo-multiplier tube, the output of which charges an analytical capacitor. At the end of a specified arcing time, controlled by a clock or by the reading of a reference channel, the voltage on the analytical capacitor may be displayed on a digital voltmeter to give a direct reading of the content concentration of that element.

The spectrometer may be a single analytical channel instrument for analysing each element separately. Alternatively the spectrometer may have facility to analyse for a specified plurality of elements simultaneously.

We have found under experimental conditions that it is possible with the apparatus illustrated to analyse steel tubes for the presence of e.g. molybedenum, chromium, manganese and vanadium to within 10% of their content concentration. Nickel and Niobium have also been determined.

By the apparatus and method of the present invention there is provided a convenient method of analysing metal articles under plant conditions. We have found it possible to carry out analysis tests in very short measurement times. Typically these times are about 10 seconds in total for each test and can in some cases be well below 10 seconds. We have found it possible to carry out the analysis on unprepared metal surface in testing time of this order. In these circumstances the only effect on the article tested is to leave a slight burn mark from the arc discharge.

We claim:

1. Apparatus for analysing the metal content of a solid metal article comprising a portable probe assembly adapted for application to the article to be analysed, a discharge electrode carried by the probe assembly, means for initiating and maintaining an electrical discharge between the electrode and the article, a remote radiation spectrometer, and a flexible radiation guide connecting the probe assembly to the radiation spectrometer and providing a flexible radiation path from the discharge to the spectrometer to enable spectroscopic analysis by the spectrometer of radiation emitted from the discharge, the portable probe assembly including a casing having a mouth for facing to the article to be tested, and a spacing member disposed at the mouth of the casing for contacting the article and locating the assembly in relation thereto, the assembly being so disposed and arranged that in operation thereof with the spacing member contacting the article, the electrode is at an optimum discharge spacing from the article.

2. Apparatus as claimed in claim 1 wherein the electrode is spring loaded to said optimum discharge spacing away from the article, and is capable of movement against the spring loading to contact the article for initiation of the discharge.

3. Apparatus as claimed in claim 1 wherein the means for initiating and maintaining an electrical discharge is adapted to provide a high energy low voltage D.C. arc discharge.

4. Apparatus as claimed in claim 3 wherein the means for initiating and maintaining the arc discharge is adapted to provide at the electrode during arcing a current of up to 10 amps at 25 to 50 volts on closed circuit.

5. Apparatus as claimed in claim 1 wherein the radiation spectrometer is an optical spectrometer and the radiation guide is an optical light guide.

6. Apparatus as claimed in claim 1 wherein the light guide comprises a flexible guide of optical glass fibres.

7. Apparatus as claimed in claim 1 wherein the spacing member defines with the article in use an electrical discharge chamber.

8. A method of analysing the metal content of a solid metal article comprising the steps of placing a portable probe assembly carrying a discharge electrode against the article such that the discharge electrode is located at an optimum discharge distance from the article, striking an electrical discharge between the electrode and the article, transmitting radiation emitted by the discharge via a flexible radiation guide to a remote radiation spectrometer, and analysing the output radiation from the radiation guide by the spectrometer.

9. A method as claimed in claim 8 wherein the electrical discharge is a high energy low voltage D.C. arc discharge.

10. A method as claimed in claim 9 wherein the arc discharge carries a current of up to 10 amps at 25 to 50 volts on closed circuit.

11. A method as claimed in claim 8 wherein the analysis of radiation includes the steps of measuring the spectral line intensity of a constituent element of the article.

* * * * *